US012788593B2

(12) United States Patent
Hettich et al.

(10) Patent No.: US 12,788,593 B2
(45) Date of Patent: Nov. 10, 2026

(54) TIBIAL TRIAL IMPLANT

(71) Applicant: Aesculap AG, Tuttlingen (DE)

(72) Inventors: Georg Hettich, Freiburg (DE); Lucy Mayrhofer, Dusslinge (DE)

(73) Assignee: Aesculap AG, Tuttlingen (DE)

( * ) Notice: Subject to any disclaimer, the term of this patent is extended or adjusted under 35 U.S.C. 154(b) by 371 days.

(21) Appl. No.: 18/634,050

(22) Filed: Apr. 12, 2024

(65) Prior Publication Data

US 2024/0358526 A1 Oct. 31, 2024

(30) Foreign Application Priority Data

Apr. 26, 2023 (DE) ..................... 10 2023 110 667.8

(51) Int. Cl.

| | |
|---|---|
| ***A61F 2/46*** | (2006.01) |
| ***A61F 2/30*** | (2006.01) |
| ***A61F 2/38*** | (2006.01) |
| ***B33Y 80/00*** | (2015.01) |

(52) U.S. Cl.

CPC .......... *A61F 2/4684* (2013.01); *A61F 2/3859* (2013.01); *A61F 2/389* (2013.01); *B33Y 80/00* (2014.12); *A61F 2002/30985* (2013.01)

(58) Field of Classification Search

CPC ....... A61F 2/4684; A61F 2/3859; A61F 2/389
See application file for complete search history.

(56) References Cited

U.S. PATENT DOCUMENTS

| | | | | |
|---|---|---|---|---|
| 5,865,848 | A | 2/1999 | Baker | |
| 7,632,314 | B2 * | 12/2009 | Dietz ..................... | A61B 90/00 623/20.33 |
| 10,188,530 | B2 | 1/2019 | Claypool et al. | |
| 2020/0289291 | A1 | 9/2020 | Cardamone et al. | |

FOREIGN PATENT DOCUMENTS

| | | | | |
|---|---|---|---|---|
| CN | 209450725 U | * 10/2019 | ............. | A61B 90/06 |
| CN | 111494065 A | * 8/2020 | ............. | A61B 90/06 |
| DE | 102020208501 A1 | 1/2022 | | |
| EP | 4011334 A1 | 6/2022 | | |
| EP | 4082485 A1 | 11/2022 | | |
| WO | 2012004580 A1 | 1/2012 | | |

* cited by examiner

*Primary Examiner* — Eduardo C Robert
(74) *Attorney, Agent, or Firm* — Christopher A. Rothe; CM Law

(57) ABSTRACT

A tibial trial implant for use in a knee joint replacement operation includes an articulation component with an articulation surface for articulation with a femoral component, at least one support component having a bearing surface configured for bearing on a tibial plateau, a top side forming a ramp inclined relative to the bearing surface, and a guide device having a guide track parallel to the ramp. A bottom side of the articulation component has a support surface inclined parallel to the ramp. The articulation component is held on the guide device and supported with its support surface on the ramp in a manner linearly movable along the guide track relative to the support component. Relative movement between the articulation component and support component changes a proximodistal distance between the articulation surface of the articulation component and bearing surface of the support component.

17 Claims, 8 Drawing Sheets

TIBIAL TRIAL IMPLANT

CROSS-REFERENCE TO RELATED APPLICATIONS

This application claims priority under 35 U.S.C. § 119 to German Application No. 10 2023 110 667.8, filed on Apr. 26, 2023, the content of which is incorporated by reference herein in its entirety.

FIELD

The disclosure relates to a tibial trial implant for use in a knee joint replacement operation.

BACKGROUND

In a knee joint replacement operation or total knee arthroplasty (TKA), joint surfaces of the femur and of the tibia are replaced by artificial joint surfaces of a knee joint prosthesis. Knee joint prostheses typically comprise a femoral implant, a tibial implant and a meniscus component, often also referred to as a gliding surface. The femoral implant is implanted at the distal end of the femur. The tibial implant is implanted at the proximal end of the tibia. The meniscus component is arranged proximodistally between the tibial implant and the femoral implant. In order to ensure correct functioning of the artificial joint replacement, said implants have to be precisely positioned in a defined manner as regards their location and orientation in relation to the anatomic body axes of the patient. In addition to the precise positioning, it is important that the implants are each selected and implanted with dimensions appropriate to the patient's anatomy. As regards the meniscus component, its proximodistal height in particular is an essential criterion.

The tibial trial implant is used for intraoperative determination of the required proximodistal height of the meniscus component that is to be implanted. Specifically, the tibial trial implant is used to test an optimal ligament tensioning and joint line in the case of a femoral implant that has already been implanted. The meniscus component is selected and implanted according to the results of this testing. Said testing can be carried out, for example, using different meniscus test components with different defined heights.

EP 4 011 334 A1 discloses a tibial trial implant with an upper plate and a lower plate. The upper plate has a proximal articulation surface for articulation with a femoral component. The lower plate has a distal bearing surface for bearing on a tibial plateau. A height adjustment mechanism is arranged between the upper plate and the lower plate. The height adjustment mechanism serves to adjust a proximodistal distance between the articulation surface of the upper plate and the bearing surface of the lower plate and thus the proximodistal height of the trial implant. The height adjustment mechanism has two scissor joint mechanisms coupled to each other.

Another tibial trial implant is known from DE 10 2020 208 501 A1. The known tibial trial implant has a top part with a proximally arranged articulation surface for articulating interaction with a femoral component. The bottom part is provided for tibial fixation. Between the top part and the bottom part, a height adjustment mechanism is arranged by means of which the top part is guided movably in a vertical direction relative to the bottom part. The movement of the top part in turn serves to adjust said proximodistal distance and thus the height of the trial implant. The height adjustment mechanism has a cam gear with a rotating drive wheel.

Another tibial trial implant is known from EP 4 082 485 A1. This trial implant has a bearing component with a proximal articulation surface and a distal surface. In addition, a plate component with a proximal surface and with a distal attachment surface is present. Arranged between the bearing component and the plate component is a distance adjustment arrangement which on the one hand engages releasably with the bearing component and on the other hand engages releasably with the plate component and couples the two components to each other with limited mobility in the proximodistal direction. Furthermore, the known tibial trial implant has a plurality of spacers or shims which, in order to adjust the proximodistal height, can be inserted into the distance adjustment arrangement between the bearing component and the plate component. Different spacers have different proximodistal thicknesses. Depending on the selection of the spacer, a different proximodistal height of the trial implant can be set.

SUMMARY

The object of the disclosure is to provide a tibial trial implant which has a simplified structure compared to the prior art and is easy to use.

The tibial trial implant according to the disclosure has an articulation component and at least one support component. The articulation component has a proximal articulation surface and a distal bottom side. The proximal articulation surface is configured for articulation with a femoral component. The at least one support component has a distal bearing surface, a proximal top side and a guide device. The distal bearing surface is configured for bearing on a tibial plateau. The proximal top side forms a ramp that is inclined relative to the distal bearing surface. The guide device has a guide track extending longitudinally parallel to the ramp. The bottom side of the articulation component has a support surface inclined parallel to the ramp. The articulation component is held on the guide device and is supported with its support surface on the ramp in a manner linearly movable along the guide track relative to the support component. A relative movement between the articulation component and the support component therefore causes a change in a proximodistal distance between the articulation surface of the articulation component and the bearing surface of the support component. By virtue of the disclosure, the tibial trial implant has a particularly simple structure. In particular, it is possible to do without complex height adjustment mechanisms and the use of different meniscus test components with different heights. Instead, it is provided that the at least one support component can be pushed in the manner of a wedge between the tibial plateau and the articulation component. For this purpose, the top side of the support component is inclined relative to the distal bearing surface and forms said ramp. The distal bottom side of the articulation component extends parallel to the ramp and is thus inclined accordingly. To prevent undefined relative movements between the articulation component and the support component, the guide device is provided. The guide device secures the articulation component and the support component to each other linearly movably along the guide track extending parallel to the ramp and thus also to the support surface. A relative movement between the articulation component and the support component along the guide track thus causes a change in the proximodistal distance. The greater the relative movement, the greater the change in distance. Starting from an (intraoperative) situation in which the articulation component is locally fixed, the support component can be inserted to a greater or lesser extent between the articulation component and the tibial plateau. Depending on the advance of the support component, the articulation component is moved proximally to a greater or lesser extent in the direction of the femoral component, and thus the proximodistal distance between the bearing surface of the support component, and thus the tibial plateau, and the articulation surface is changed. The femoral component and the tibial plateau are not part of the tibial trial implant. The femoral component can be a natural distal femur or a femoral implant component. The tibial plateau can be formed by a resection surface on the proximal tibia or by an artificial platform surface attached to the resection surface. The bearing surface configured to bear on the tibial plateau is preferably flat and parallel to an anteroposterior and mediolateral transverse plane. The ramp formed by the top of the support component is inclined relative to the transverse plane, such that, in particular in a mediolateral or anteroposterior viewing direction, a wedge-shaped design of the support component is obtained. In a relative movement between the tibial component and support component, the support surface of the articulation component and the ramp slide against each other. At the same time, the two components are guided by means of the guide device. The guide device is arranged and/or formed at least in sections on the support component and, for guiding purposes, interacts with a portion of the articulation component that is configured for this purpose. In one embodiment, the tibial trial implant has exactly one support component, so that an overall two-part structure is provided. In a further embodiment, the tibial trial implant has exactly two support components, so that an overall three-part structure of the trial implant is provided.

The positional and directional designations used in this description relate to the body of a patient, in particular to the tibia, and are to be understood according to their usual anatomical meaning. Consequently, “anterior” denotes front or lying to the front, “posterior” denotes rear or lying to the rear, “medial” denotes inner or lying to the inside, “lateral” denotes outer or lying to the outside, “proximal” denotes towards the centre of the body, and “distal” denotes away from the centre of the body. Furthermore, “proximodistal” denotes along, preferably parallel to, a proximal-distal axis, “anteroposterior” denotes along, preferably parallel to, an anterior-posterior axis, and “mediolateral” denotes along, preferably parallel to, a medial-lateral axis. The aforementioned axes are orthogonal to one another and can of course be understood in relation to X, Y and Z axes not associated with the anatomy of the patient. For example, the proximodistal axis can alternatively be called the Z axis. The mediolateral axis can be called the Y axis. The anterior-posterior axis can be called the X axis. For the sake of better understanding and simplicity of the designations, the aforementioned anatomical positional and directional designations are primarily used in the following. In addition, designations such as “top side” are used in relation to a distal direction of viewing. On the other hand, designations such as “bottom side” are used in relation to a proximal direction of viewing.

In one embodiment of the disclosure, the ramp and/or the support surface is flat and has a surface profiling configured to counteract slipping of the articulation component from the ramp. This prevents an unwanted change of a proximodistal distance once the latter has been set. The surface profiling causes increased friction between the ramp and the support surface. The surface profiling preferably has protruding elevations and/or introduced recesses in the normal direction of the ramp and/or support surface. On account of the flat design of the ramp and/or of the support surface, a stepless change of the proximodistal distance is preferably possible.

In one embodiment of the disclosure, the ramp and the support surface are each provided with a sequence of steps, whereby the relative movement between the articulation component and the support component causes a step-by-step change in the proximodistal distance. The steps each have a height extending in the proximodistal direction. The steps rise from one (low) end of the ramp in the direction of an opposite (high) end. The same applies, mutatis mutandis, to the steps of the support surface. Preferably, the steps are each bevelled, such that the support surface and the ramp, despite the presence of steps, can slide against each other along the guide track.

In one embodiment of the disclosure, the steps each have a proximodistal height of between 1 mm and 3 mm, preferably of 2 mm, with at least four steps being present in each case. This results in an at least 4-step adjustment range for the proximodistal distance. A height of 2 mm has proven particularly advantageous for the steps. On the one hand, the abovementioned height is sufficiently small to be able to set even small changes in the distance. On the other hand, a height of 2 mm per step permits a sufficiently large adjustment range in the case of at least four steps. The height of the individual steps and the achievable total height of the tibial trial implant are preferably tailored to the available meniscus components of different heights, which components are usually available in heights of 10 mm, 12 mm, 14 mm, 16 mm, 18 mm, 20 mm, 22 mm and 24 mm.

In one embodiment of the disclosure, the steps of the ramp each have a convex protuberance, and the steps of the support surface each have a complementary concave indentation, wherein the protuberances and the indentations engage releasably in one another, thereby counteracting an unwanted relative movement between the articulation component and the support component. The interlocking of the protuberances and indentations counteracts unwanted relative movements between the complementary steps and thus between the articulation component and the support component. This prevents unwanted changes in the height of the tibial trial implant. For the desired relative movement, the engagement between the indentations and the protuberances can be overcome manually, for example by lifting the articulation component slightly from the support component. It will be understood that a reverse arrangement of protuberances and indentations can also be provided. Consequently, in one embodiment, the concave indentations are present on the steps of the ramp and the convex protuberances are present on the steps of the support surface.

In one embodiment of the disclosure, the ramp and/or the support surface has a longitudinal inclination of 10° to 45°, preferably of 15° to 30°, particularly preferably of 20°. The longitudinal inclination is measured relative to the bearing surface and thus also to the tibial plateau. Alternatively or additionally, the longitudinal inclination is measured relative to an imaginary transverse plane. The steeper the longitudinal inclination, the greater a ratio between the relative movement of the tibial component and support component and the change in the proximodistal distance. A small relative movement therefore causes a relatively large change in the proximodistal distance. At the same time, a relatively large amount of force is required to advance the support component. The opposite is true, mutatis mutandis, for shallow longitudinal slopes. Against this background, a longitudinal inclination in the range of 15 to 30° has proven advantageous, with 20° being considered an optimum.

In one embodiment of the disclosure, the ramp and the support surface are inclined longitudinally in an anteroposterior direction. In other words, the ramp rises along an anteroposterior axis, and the same applies analogously to the support surface. Since the guide track extends parallel to the ramp and thus also to the support surface, what is said above also applies to its longitudinal inclination. In this embodiment, the at least one support component is moved in the anteroposterior direction relative to the articulation component in order to change the proximodistal distance. Preferably, a relative advance of the support component directed from anterior to posterior causes an increase in the proximodistal distance. A decrease is obtained in a kinematically reverse manner.

In one embodiment of the disclosure, the ramp and the support surface are inclined mediolaterally. Consequently, the ramp rises along a mediolateral axis. This also applies, mutatis mutandis, to the support surface. In this embodiment, the at least one support component can be moved in the mediolateral direction relative to the articulation component in order to change the proximodistal distance during an operation. In other words, a "lateral" relative advance of the support component is provided. If the tibial trial implant has exactly one support component, the latter, in this embodiment of the disclosure, can be arranged laterally or medially of a sagittal median longitudinal plane of the articulation component. If the support component is arranged laterally, a medial advance preferably causes an increase in the proximodistal distance. If the support component is instead arranged medially, a lateral advance preferably causes an increase in the proximodistal distance. To reduce the proximodistal distance, the support component is displaced kinematically in the opposite direction.

In one embodiment of the disclosure, two support components are present and are arranged on both sides of a sagittal median longitudinal plane of the articulation component, wherein the two support components, in order to change the proximodistal distance, are movable mediolaterally in opposite directions relative to the articulation component. In this embodiment, the support components can also be referred to as a first support component and a second support component. The first support component is preferably arranged on a lateral side of the sagittal median longitudinal plane. The second support component is preferably arranged on a medial side of the sagittal median longitudinal plane. To change the proximodistal distance, the two support components are moved in opposite directions to each other relative to the articulation component. In particular, this embodiment permits a medially and laterally quantitatively different change of the proximodistal distance. For example, the articulation surface can be raised further proximally on a medial side than on a lateral side, or vice versa. This makes it possible to take better account of the patient's anatomy.

In one embodiment of the disclosure, the guide device has at least one guide slot in which at least one guide pin of the articulation component engages along the guide track in a sliding motion. The guide slot is introduced into the support component and defines the guide track. If the ramp and the support surface are each provided with a sequence of steps, this preferably also applies to the guide slot. In this case, the steps of the guide slot are offset in parallel to the steps of the ramp. The at least one guide pin is arranged and/or formed on the articulation component. The guide pin engages movably in the guide slot along the guide track. In one embodiment, the guide slot is open at one end and has, at its open end, an insertion opening for the guide pin. For assembly of the tibial trial implant, the guide pin can be inserted through the insertion opening into the guide slot. In a further embodiment, the guide slot is closed at its opposite ends. For assembly, the guide pin in this embodiment can be movable relative to the articulation component. Alternatively, an additive manufacture can be provided in accordance with an embodiment described in more detail below. In one embodiment, two guide slots extending parallel to each other are provided, and correspondingly two guide pins.

In one embodiment of the disclosure, the guide slot has, at one end of the guide track, an insertion opening which, starting from the bearing surface, opens into the guide slot substantially perpendicularly to the guide track, and through which the at least one guide pin is insertable into the guide slot. For the insertion of the guide pin, the articulation component can be attached to the support component with its articulation surface and its bottom side oriented the other way round, i.e. with the bottom side oriented approximately proximally. After insertion of the at least one guide pin into the guide slot, the articulation component can be rotated through 180° so that the articulation surface and the bottom side readopt their intended orientation. As a result of this special assembly or "insertion movement", the mobility between the articulation component and the support component is possible only along the guide track. This prevents unwanted separation of the components, especially in the anteroposterior and/or proximodistal direction.

In one embodiment of the disclosure, the support surface is recessed proximally into the bottom side of the articulation component and is bounded by opposite wall sections, which in each case bear with a form-fit on the support component perpendicularly to the guide track and perpendicularly to a proximodistal axis. The aforementioned form-fit achieves further improved guiding of the relative movement between the tibial component and the support component. The wall sections each bear laterally on the support component, preferably the ramp.

In one embodiment of the disclosure, the articulation component has a recess which extends proximodistally from the articulation surface to the support surface and which divides the articulation surface and the support surface into in each case a medial surface section and a lateral surface section. In this embodiment, the articulation surface thus comprises a medial articulation surface section and a lateral articulation surface section. These two sections are arranged lying opposite each other on both sides of the recess and are spaced apart from each other by a mediolateral dimension of the recess. The same applies, mutatis mutandis, for the support surface, so that a medial support surface section and a lateral support surface section are present. In particular, the recess permits improved visibility of the support component arranged distally/below the articulation component. If the support component is likewise provided with a recess, the tibial plateau can be viewed. This gives the operating surgeon improved intraoperative control.

In one embodiment of the disclosure, the at least one support component has a recess which extends proximodistally through the ramp and which divides the ramp into two ramp sections, which are spaced apart from each other laterally, in particular mediolaterally or anteroposteriorly. On the one hand, the ramp extending through the recess allows a saving in material and thus an associated saving in production costs and weight. If the articulation component according to the preceding description is provided with a recess, the recess of the support component allows improved visibility of the tibial plateau arranged distally/below the support component. If the ramp has an anteroposterior longitudinal inclination, the two ramp sections are spaced apart mediolaterally from each other by the dimensions of the recess. Consequently, it is also possible to refer to them as medial ramp section and lateral ramp section. If the ramp has a mediolateral longitudinal inclination, the two ramp sections are spaced apart anteroposteriorly from each other by the dimensions of the recess. In this case, it is also possible to refer to them as anterior ramp section and posterior ramp section. Both ramp sections extend longitudinally. The recess is preferably open at one end in the longitudinal direction of the ramp, the opening preferably being arranged at a low end of the ramp.

In one embodiment of the disclosure, the at least one support component, seen in the proximal and/or distal viewing direction, has a U-shaped configuration, wherein the two ramp sections each form an elongate leg of the U-shape. The U-shape of the support component permits ergonomic handling in particular. During the use of the tibial trial implant, the U-shaped support component can be gripped between the fingers of one hand in the region of a transverse leg connecting the two elongate legs. This is ergonomically advantageous.

In one embodiment of the disclosure, the articulation component and the at least one support component are each manufactured from a biocompatible plastic material. Biocompatible plastic materials are known as such to a person skilled in the relevant art. The use of such plastic materials for the articulation component and the support component offers particular advantages. Preferably, the articulation component and the at least one support component are each manufactured in one piece from said plastic material. The manufacture can be carried out, for example, by means of injection moulding. In a further embodiment, additive manufacturing is carried out instead.

In one embodiment of the disclosure, the articulation component and the at least one support component are additively manufactured by means of a single 3D printing process, whereby the articulation component and the at least one support component are connected non-releasably to each other via the guide device and are movable relative to each other. In this embodiment of the disclosure, the articulation component and the at least one support component are secured captively to each other. On account of the single 3D printing process, no separate assembly step is required for connecting the articulation component to the at least one support component. Preferably, the 3D printing is carried out using a biocompatible plastic material.

Further advantages and features of the disclosure will become clear from the following description of preferred exemplary embodiments of the disclosure that are shown in the drawings.

DETAILED DESCRIPTION

According to FIGS. 1 to 6, a tibial trial implant 1 is provided for use in a knee joint replacement operation. The tibial trial implant 1 is used to determine a proximodistal height of a tibial implant and is often referred to in medical terminology as a test gliding surface.

Figure 7:
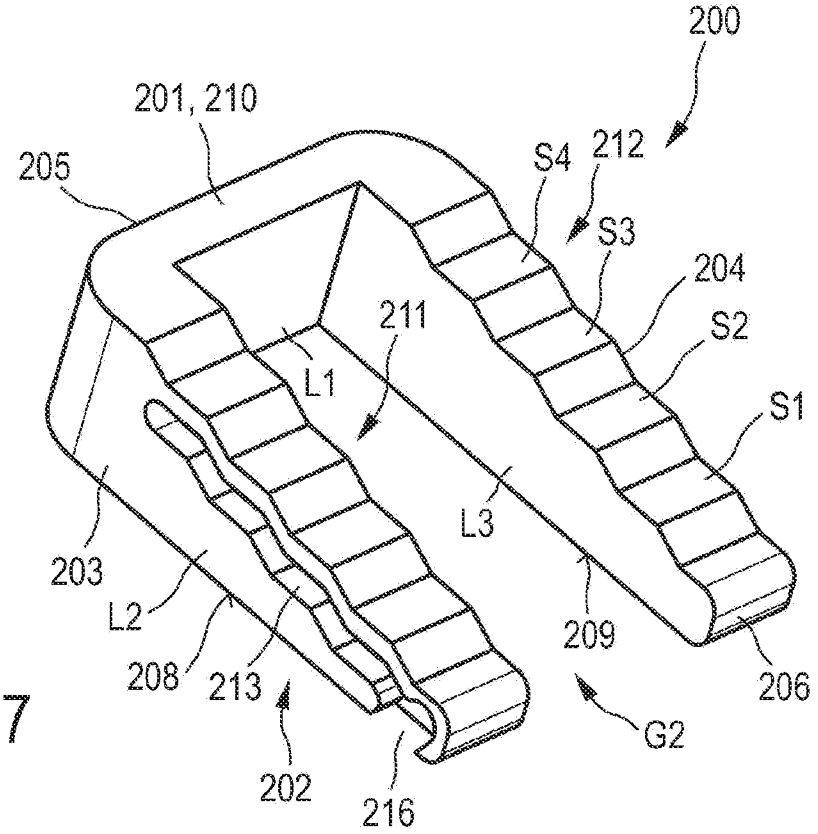
FIG. 7 shows the support component of the tibial trial implant according to FIGS. 1 to 6 in a schematic perspective view.
Figure 8:
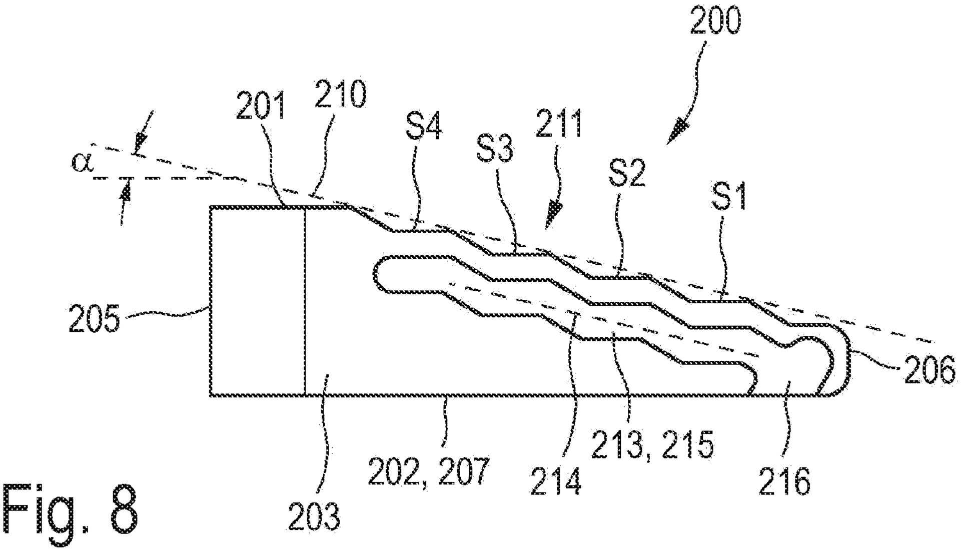
FIG. 8 shows the support component according to FIG. 7 in a schematic side view.

The tibial trial implant 1 has an articulation component 100 and a support component 200. The articulation component 100 is shown separately in FIGS. 9 to 11. The support component is shown separately in FIGS. 7 and 8.

The articulation component 100 has a proximal top side 101, a distal bottom side 102, a medial outer side 103, a lateral outer side 104, an anterior front side 105 and a posterior back side 106. The proximal top side 101 and the distal bottom side 102 lie opposite each other along a proximodistal axis. The medial outer side 103 and the lateral outer side 104 lie opposite each other along a mediolateral axis. The anterior front side 105 and posterior back side 106 lie opposite each other along an anteroposterior axis. These axes are orthogonal to each other.

The top side 101 of the articulation component 100 has an articulation surface 107, which is configured for articulation with a femoral component F. The femoral component F is shown schematically and in section in FIG. 2 and can be formed by a natural distal femur or a femoral implant.

In the embodiment shown, the articulation surface 107 is formed by two articulation surface sections 108, 109, which are arranged opposite each other in relation to an imaginary sagittal median longitudinal plane of the articulation component 100 and can also be referred to as medial articulation surface section 108 and lateral articulation surface section 109.

Between the articulation surface sections 108, 109, the articulation component 100 in the present case has a continuous proximodistal recess G1. The recess G1 divides the articulation surface 107 into said surface sections 108, 109 and is to be regarded as optional. The recess G1 is therefore not present in all embodiments.

Figure 9:
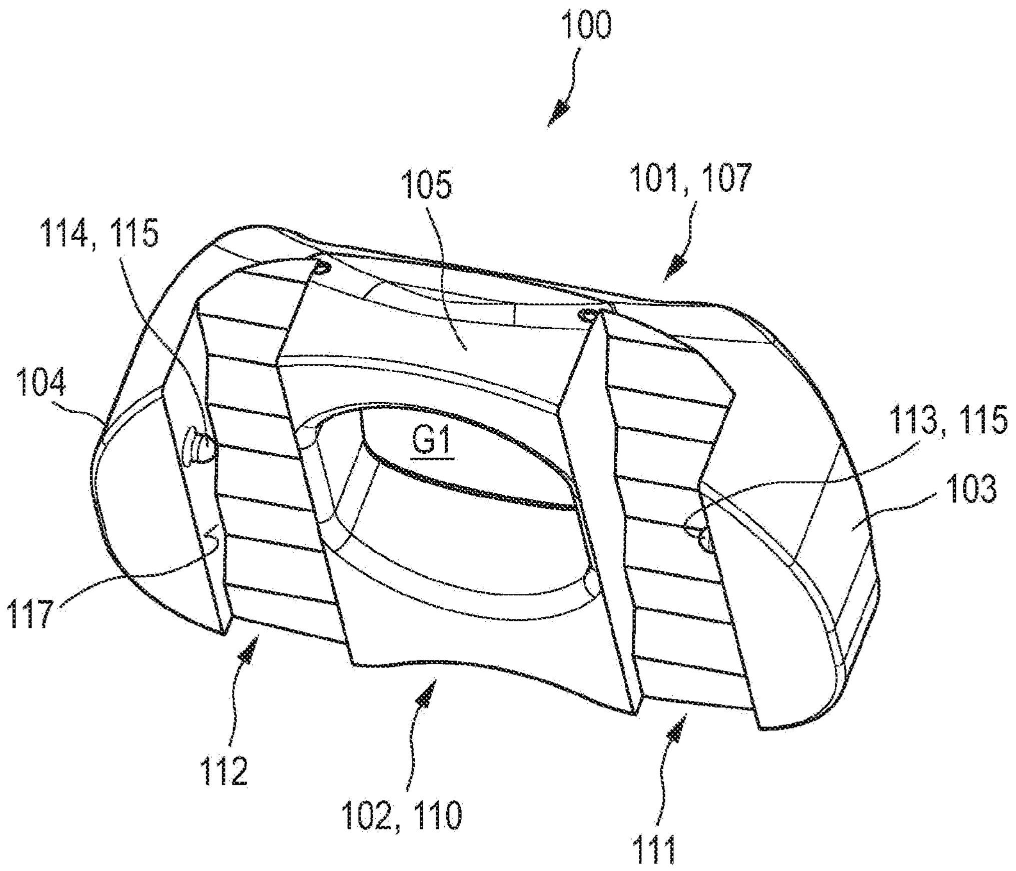
FIG. 9 shows a schematic perspective view of the articulation component of the tibial trial implant according to FIGS. 1 to 6.

The bottom side 102 of the articulation component 100 has a support surface 110 (see in particular FIG. 9). In the embodiment shown, the support surface 110 has two mediolaterally spaced apart support surface sections 111, 112, which can also be referred to as medial support surface section 111 and lateral support surface section 112. Such a subdivision/division of the support surface 110 is not provided in all the embodiments and is optional. Said recess G1 is arranged, with respect to the mediolateral axis, between the two support surface sections 111, 112.

The support component 200 has a proximal top side 201, a distal bottom side 202, a medial outer side 203, a lateral outer side 204, an anterior front side 205 and a posterior back side 206. The proximal top side 201 and the distal bottom side 202 lie opposite each other along the proximodistal axis. The medial outer side 203 and the lateral outer side 204 lie opposite each other along the mediolateral axis. The anterior front side 205 and the posterior back side 206 lie opposite each other along the anteroposterior axis.

Furthermore, the support component 200 has a bearing surface 207 arranged on the distal bottom side 202. The bearing surface 207 is configured to bear on a tibial plateau TP. The TP is shown schematically in FIG. 2 and in the present case is formed by a resection surface of a proximal tibia T. Alternatively, the tibial plateau can be formed by a femoral implant component attached to the resection surface. The bearing surface 207 in the present case is parallel to an anteroposterior and mediolateral transverse plane.

In the embodiment shown, the support component 200 has a continuous recess G2 along the proximodistal axis. The recess G2 divides the bearing surface 207 into two mediolaterally spaced apart bearing surface sections 208, 209. The bearing surface sections 208, 209 can also be referred to as medial bearing surface section 208 and lateral bearing surface section 209. The recess G2 and the associated subdivision of the bearing surface 207 are optional and therefore not present in all the embodiments.

Furthermore, the support component 200 has a proximal ramp 210. The ramp 210 forms the top side 201 of the support component 200, and vice versa.

In the embodiment shown, the ramp 210 is longitudinally inclined along the anteroposterior axis and, starting from the posterior face 206, rises in the direction of the anterior face of the support component 200. The ramp 210 and/or the top side 201 is therefore inclined relative to the distal bearing surface 207. The longitudinal inclination of the ramp 210 in the present case is at an angle $\alpha$ with respect to the bearing surface 207 and thus also with respect to the tibial plateau TP.

The support surface 110 of the articulation component 100, already explained (see FIG. 9), extends parallel to the ramp 210 and is consequently inclined according to the ramp 210. As has already been explained, the support surface 110 in the embodiment shown is formed by the support surface sections 111, 112, which consequently likewise extend parallel to the ramp 210.

In the embodiment shown, the ramp 210 is divided into two mediolaterally spaced-apart ramp sections 211, 212 on account of the aforementioned recess G2. In other words, the ramp 210 comprises the two ramp sections 211, 212, which can also be referred to as medial ramp section 211 and lateral ramp section 212. Such a design of the ramp with a plurality of ramp sections is optional and therefore not present in all the embodiments.

Furthermore, the support component 200 has a guide device 213 with a guide track 214. The guide track 214 is indicated by a dashed line in FIGS. 2 and 8. The guide track 214 extends parallel to the ramp 210.

Figure 4:
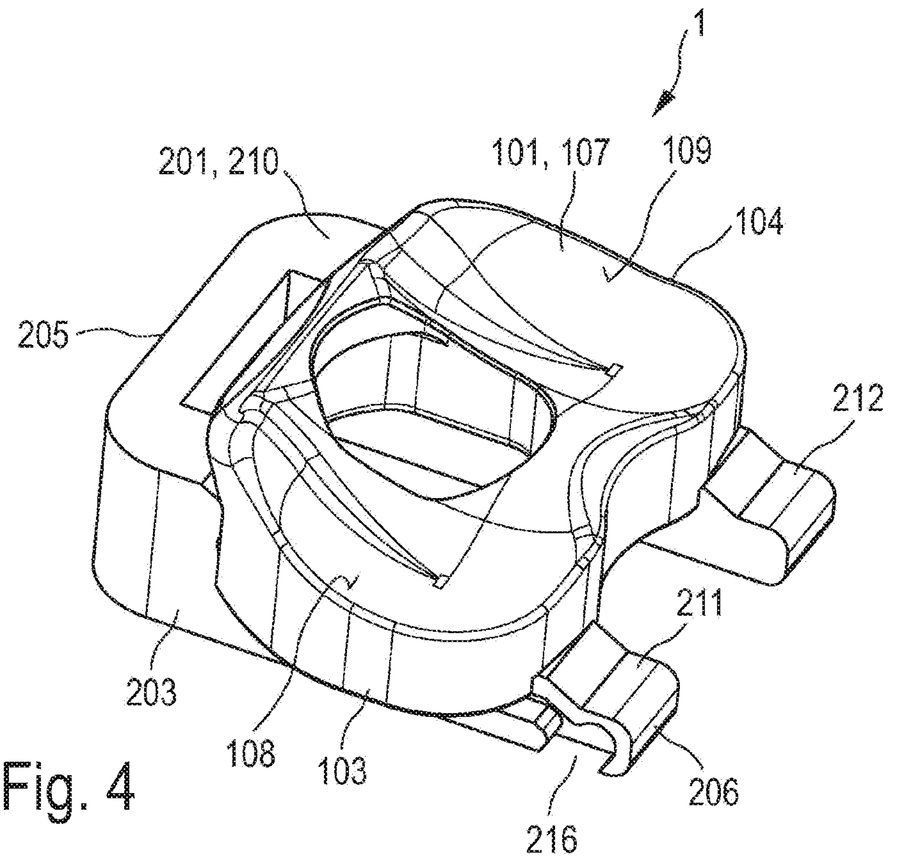
FIG. 4 shows a further schematic perspective representation of the tibial trial implant according to FIGS. 1 to 3, wherein the articulation component and the support component assume a second configuration relative to each other.
Figure 5:
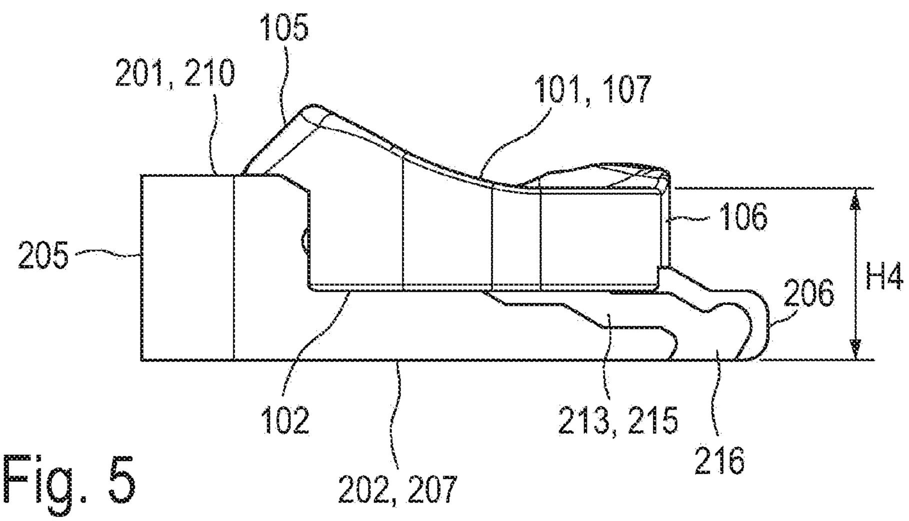
FIGS. 5 and 6 show the tibial trial implant in the configuration according to FIG. 4 in a schematic side view (FIG. 5) and a schematic plan view (FIG. 6).
Figure 6:
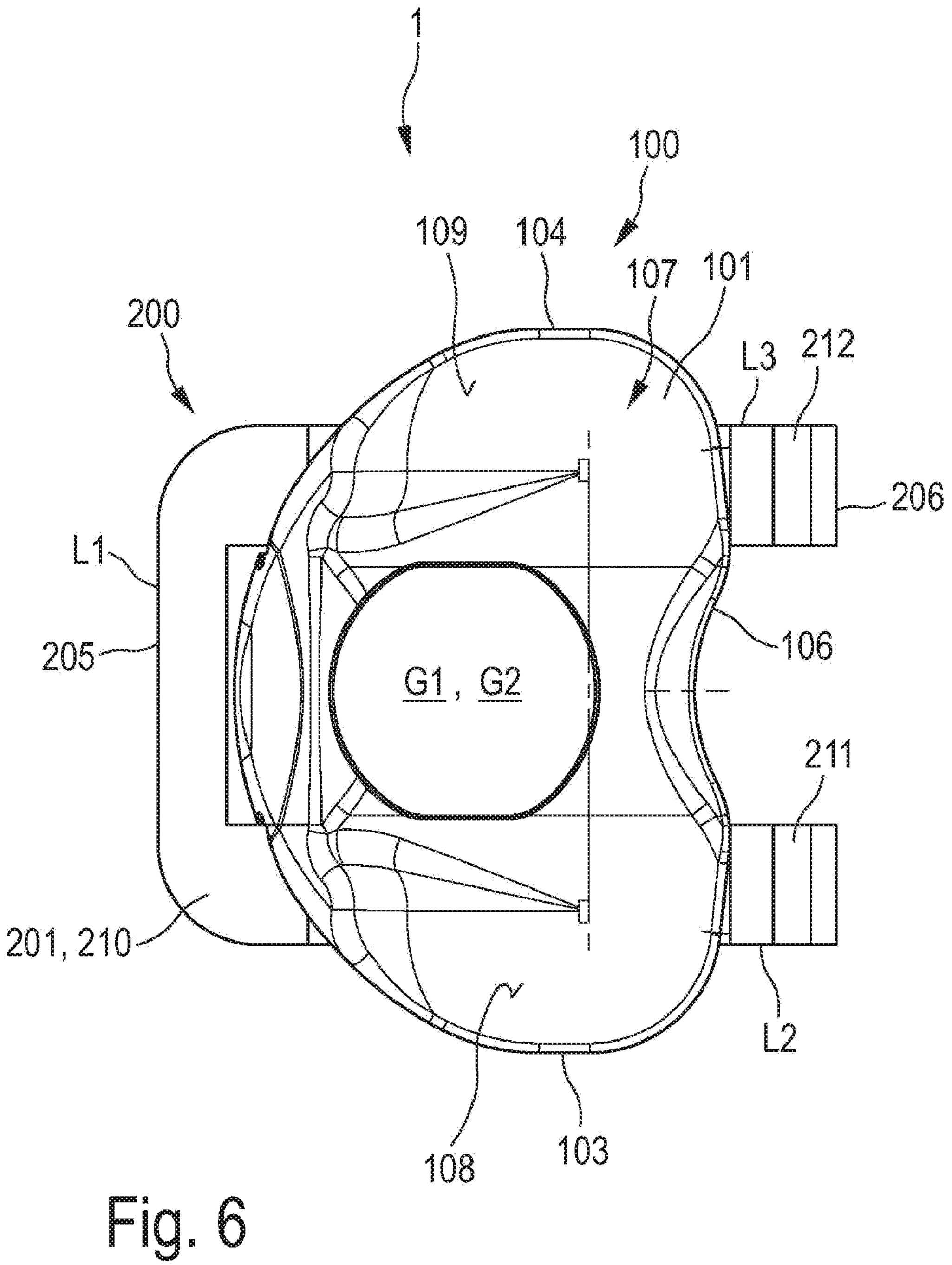

By means of the guide device 213, the articulation component 100 and the support component 200 are guided linearly on each other and are linearly movable relative to each other. The linear mobility is along the guide track 214. In this case, the articulation component 100 and the support component 200 are supported, in a manner movable relative to each other, via the support surface 110 and the ramp 210. By a relative movement between the articulation component 100 and the support component 200, a proximal distance between the articulation component 100 and the tibial plateau TP is variable. The relative mobility allows a change of the proximodistal distance between the articulation surface 107 of the articulation component 100 and the bearing surface 207 of the support component 200. In the configuration of the tibial trial implant 1 shown in FIGS. 1 to 3, a proximodistal distance H1 is set. For this purpose, the articulation component 100, more precisely the support surface 110 thereof, is in the present case supported on the ramp 210 relative to the support component 200 in a first position with respect to the guide track. The configuration of the tibial trial implant 1 shown in FIGS. 4 to 6 is adopted at a different relative positioning of the two components 100, 200. There is a different proximodistal distance H4 (see in particular FIG. 5).

The longitudinal inclination of the ramp 210 and thus also of the support surface 110 is approximately 15° in the present case. In embodiments not shown in the figures, the longitudinal inclination is between 10° and 45°.

Intraoperatively, the proximodistal distance in the embodiment shown in FIGS. 1 to 11 is changed by the operating surgeon holding the articulation component 100 stationary underneath the femoral component F and moving the support component 200 along the anteroposterior axis relative to the articulation component 100 and the tibial plateau TP. Starting from the configuration shown in FIG. 2, the proximodistal distance can be increased by advancing the support component 200 in the posterior direction between the tibial plateau TP and the articulation component 100. The ramp-shaped design of the top 201 and the complementary design of the support surface 110 result in a wedge-shaped design of the support component 200 as seen in a mediolateral viewing direction. The support component 200 can therefore also be referred to as a wedge. To reduce the proximodistal distance, the support component 200, for example starting from the configuration shown in FIG. 5, can be pulled out in the anterior direction from under the stationary articulation component 100. With the proximodistal distance thus set, the articulation component 100 and the support component 200 are always guided and/or held together in a defined manner, in particular by means of the guide device 213.

In the embodiment shown, the guide device 213 has at least one guide slot 215. The guide slot 215 is elongate and defines the guide track 214.

In the embodiment shown, the guide device 213 has two guide slots 215, with only one being shown in the figures. The guide slot 215 shown is recessed into the medial outer side 203 of the support component 200. The guide slot not shown is recessed into the lateral outer side 204.

In the embodiment shown, the articulation component 100 has at least one guide element 113, 114 for interaction with the guide device 213 of the support component 200. In the present case, a medial guide element 113 and a lateral guide element 114 are present, each designed as a guide pin 115. In this case, the medial guide element 113 engages in the medial guide slot 215 of the support component 200. The lateral guide element 114 engages in the lateral guide slot (not shown in the figures). The guide pins 115 interact with the guide slots in a sliding manner along the guide track 214.

In the embodiment shown in FIGS. 1 to 11, the guide slots 215 are open at one end. For further explanation, reference is only made below to the medial guide slot 215. What is said concerning the latter applies, mutatis mutandis, to the lateral guide slot not shown.

The guide slot 215 has an insertion opening 216 in the region of the posterior face 206. For assembling the tibial trial implant 1, the medial guide pin 113 can be inserted through the insertion opening 216 into the guide slot 215.

Figure 10:
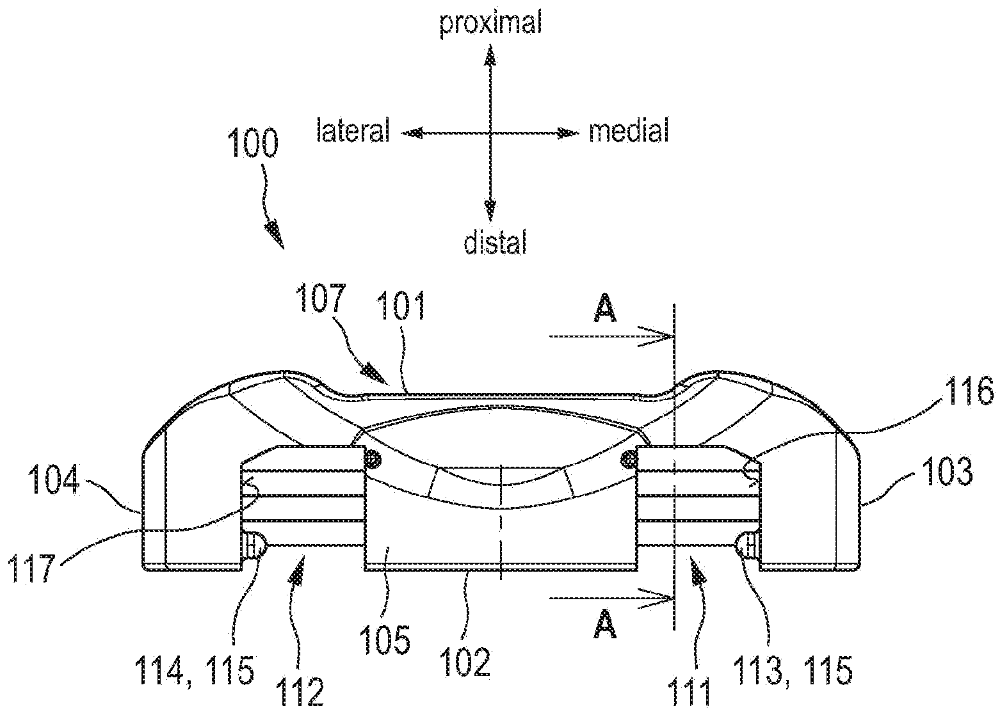
FIG. 10 shows the articulation component according to FIG. 9 in a schematic front view with a posterior viewing direction.
Figure 11:
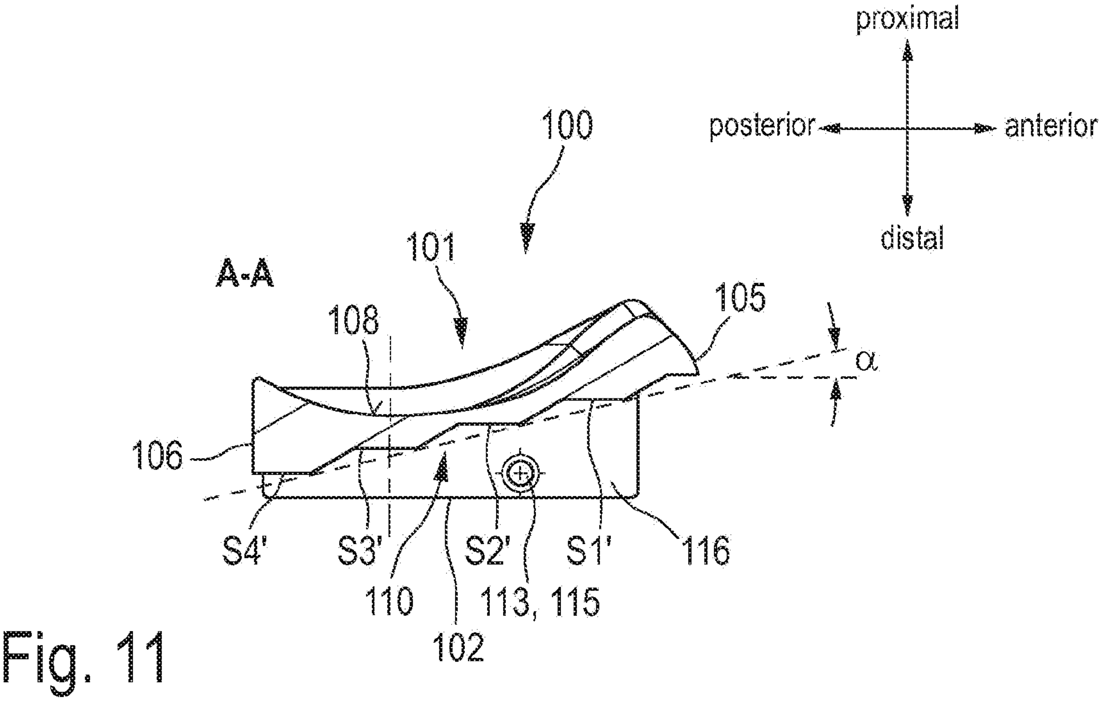
FIG. 11 shows the articulation component according to FIGS. 9 and 10 in a schematic sectional view along a section A-A according to FIG. 10.

As is shown in particular in FIGS. 9 to 11, the support surface 110, more precisely the support surface sections 111, 112 thereof, is recessed proximally into the bottom side 102 of the articulation component 100. The support surface 110 is therefore limited by wall sections 116, 117 lying mediolaterally opposite each other. Said wall sections 116, 117 can also be referred to as medial wall section 116 and lateral wall section 117. The medial wall section 116 bears with form-fit engagement on the medial outer side 203 of the articulation component in the lateral direction. The lateral wall section 117 bears with form-fit engagement on the lateral outer side 204 of the support component 200 in the medial direction.

Figure 1:
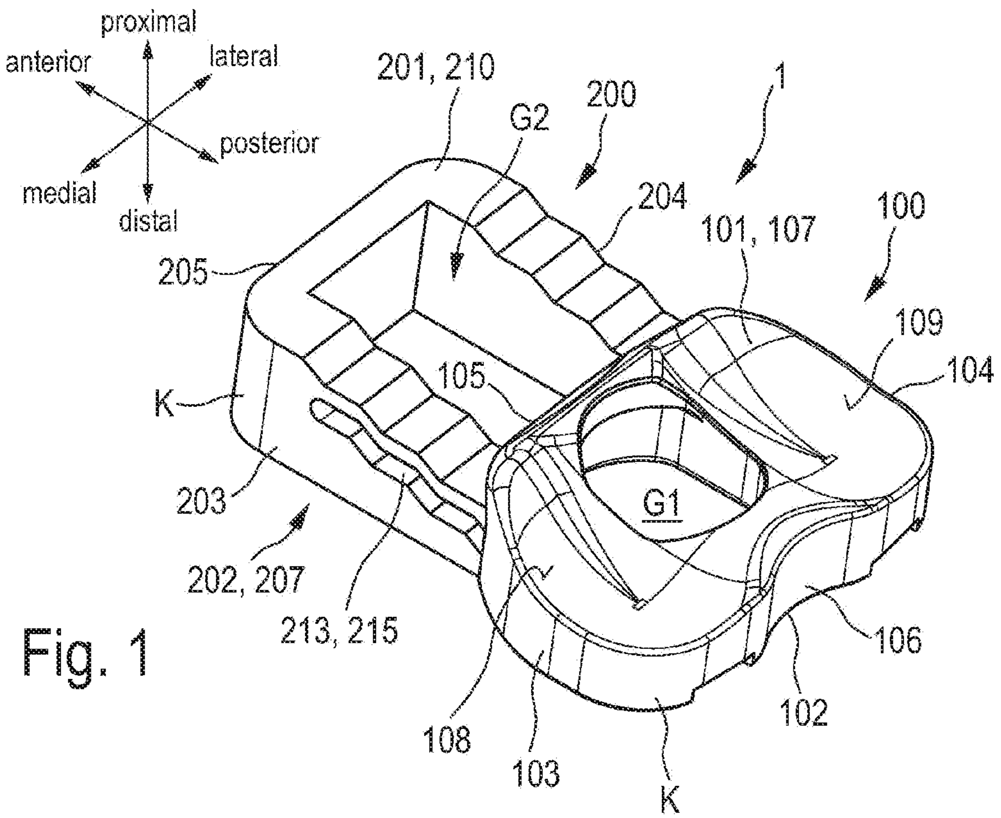
FIG. 1 shows a schematic perspective view of an embodiment of a tibial trial implant having an articulation component and a support component, wherein the articulation component and the support component assume a first configuration relative to each other.
Figure 2:
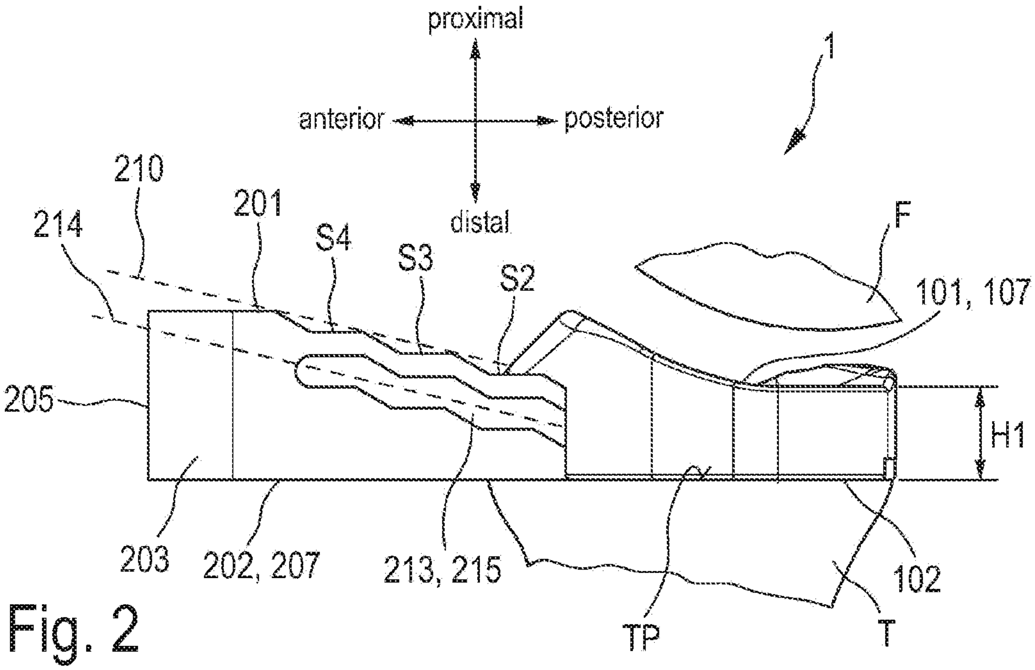
FIG. 2 shows the tibial trial implant according to FIG. 1 seen in a schematic side view.
Figure 3:
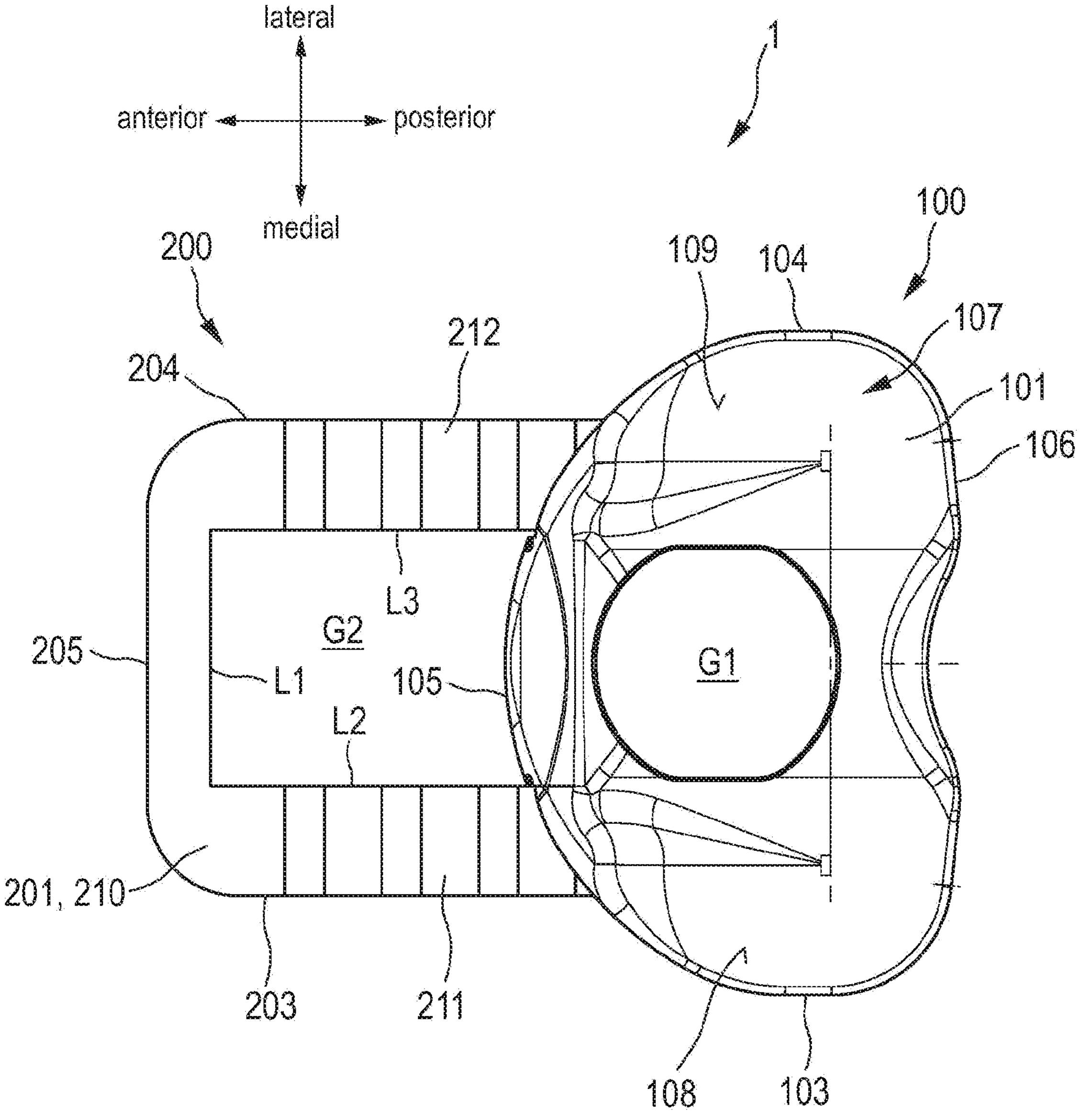
FIG. 3 shows the tibial trial implant according to FIGS. 1 and 2 in a schematic plan view with a distal viewing direction.

In the embodiment shown in FIGS. 1 to 11, the ramp 210 is provided with steps S1, S2, S3, S4 (see FIG. 2). The same applies to the support surface 110. The latter is provided with steps S1', S2', S3', S4' (see FIG. 11). On account of the specific design of the present embodiment with two ramp sections 211, 212 and two support surface sections 111, 112, all of the respective sections have a stepped design.

By virtue of the stepped design of the ramp 210 and of the support surface 110, a relative movement between the articulation component 100 and the support component 200 causes a stepwise change of the proximodistal distance. The steps S1 to S4 of the support component 200 are each assigned to a specific proximodistal distance. The step S1 defines the proximodistal distance H1 in the configuration shown in FIGS. 1 to 3. The step S4 defines the (larger) proximodistal distance H4 of the configuration shown in FIGS. 4 to 6. The other steps S2, S3 define distances lying between the two proximodistal distances H1, H4.

The steps S1 to S4 of the articulation component 200 rise proximally from the posterior face 206 in the direction of the anterior face 205. The steps S1' to S4' of the articulation component 100 rise distally from the posterior face 106 in the direction of the anterior face 105.

It will be understood that the steps S1 to S4 and the steps S1' to S4' are designed in a complementary manner.

In order to facilitate relative mobility between the two components 100, 200, the steps S1 to S4 and S1' to S4' are each bevelled. On account of the bevelling of the steps, the support component 200 can be moved, in the manner described above, anteriorly in a sliding movement relative to the articulation component 100, without the steps S1 to S4 of the support component 200 and the steps S1' to S4' of the articulation component 100 interlocking.

In the embodiment shown, the proximodistal height between the steps is 2 mm in each case. In embodiments not shown in the figures, the height is between 1 mm and 3 mm. In the present case, there are also four steps in each case.

As the support component 200 is advanced under the articulation component 100, the latter is raised proximally in steps, in each case of 2 mm, on account of the stepped design of the ramp 210 and of the support surface 110. During extraction in the anterior direction, the height of the articulation component 100 in relation to the tibial plateau TP decreases in steps of 2 mm each.

The steps S1 to S4 and S1' to S4' are preferably provided with protuberances and complementary indentations, which engage releasably in one another and counteract an unwanted relative movement between the articulation component and the support component. The abovementioned indentations and protuberances are not shown separately in the figures.

Furthermore, the articulation component 100 and the support component 200 are in the present case each made of a biocompatible plastic material K. Different manufacturing processes are conceivable. In this case, manufacture is carried out by 3D printing. In the embodiment shown in FIGS. 1 to 11, the articulation component 100 and the support component 200 are each additively manufactured separately from each other. After the additive manufacture of the two components 100, 200, they are assembled to give the tibial trial implant 1.

In the embodiment shown in FIGS. 1 to 11, the support component 200 has a U-shaped configuration. The two ramp sections 211, 212 each form an elongate leg L2, L3 of said U-shape. The U-shape moreover has another (short) leg L1. The further leg L1 is arranged extending mediolaterally at the end of the two legs L2, L3 and connects the latter to each other.

Figure 12:
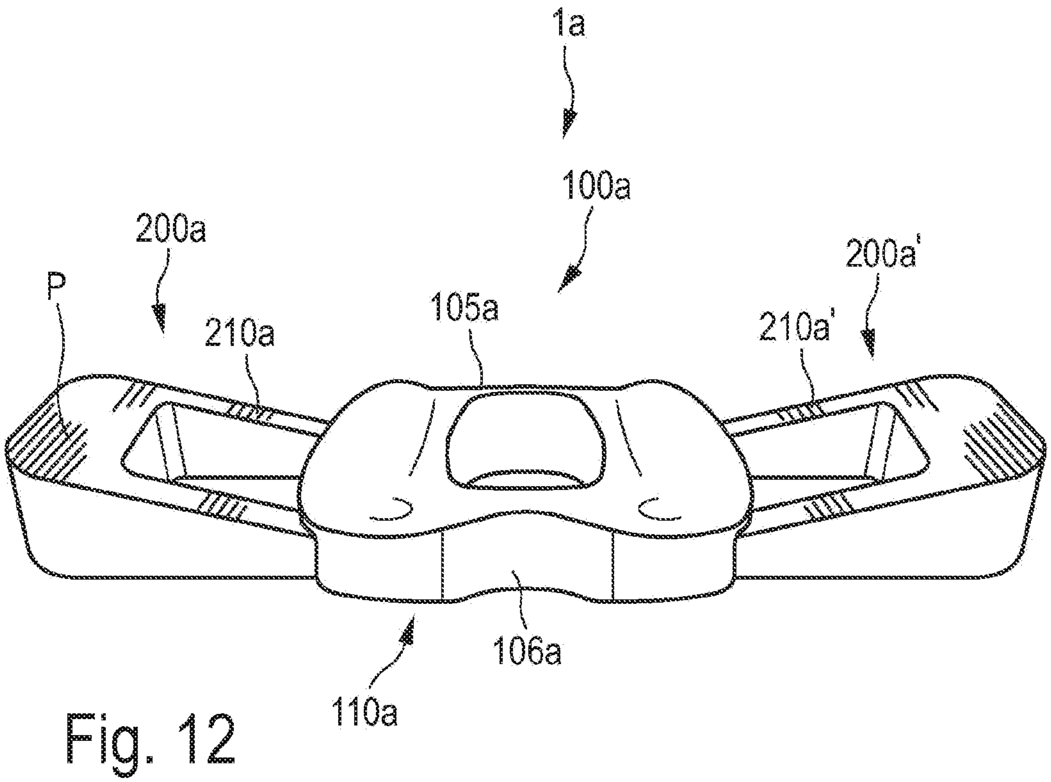
FIG. 12 shows a schematic perspective view of a further embodiment of a tibial trial implant according to the disclosure in a first configuration.
Figure 13:
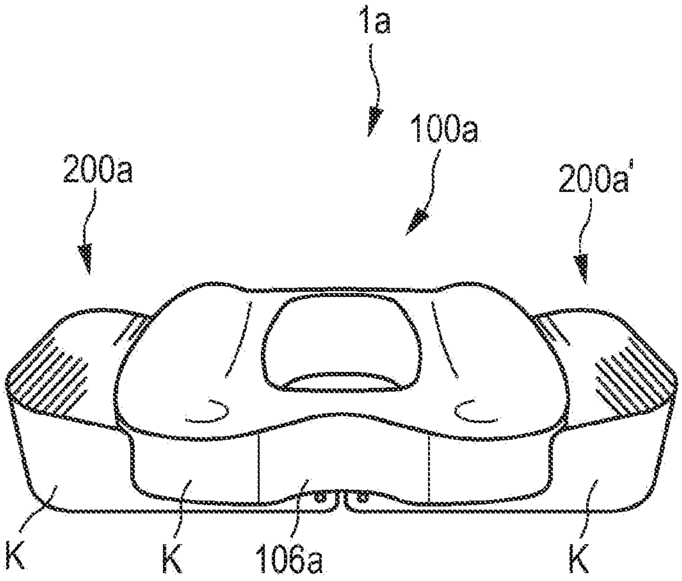
FIG. 13 shows a schematic perspective view of the embodiment of FIG. 12 in a second configuration.

FIGS. 12 and 13 show a further embodiment of a test tibial implant 1*a* according to the disclosure. In terms of its structure and function, the tibial trial implant 1*a* is largely identical to the tibial trial implant 1 according to FIGS. 1 to 11. Therefore, in order to avoid repetition, only significant differences are discussed below. Components and/or sections of the tibial trial implant 1*a* according to FIGS. 12 and 13 that have an identical function are not explained separately. Instead, in order to avoid repetition, reference is expressly made to what has already been said concerning the tibial trial implant 1 according to FIGS. 1 to 11.

The main difference of the tibial trial implant 1*a* is the presence of two support components 200*a*, 200*a*'. The two support components 200*a*, 200*a*' can also be referred to as first support component 200*a* and second support component 200*a*' and are designed identically to each other. The two support components 200*a*, 200*a*' are arranged on both sides of an imaginary sagittal median longitudinal plane of the articulation component 100*a* and are guided separately from each other in a linearly movable manner relative to the articulation component 100*a*. In this case, the inclination of the respective ramp 210*a*, 210*a*' in each case runs in the mediolateral direction, such that the support components 200*a*, 200*a*' cannot for example be pushed anteroposteriorly under the articulation component 100*a*, but instead can be pushed laterally under the articulation component 100*a* in opposite directions to each other. FIG. 12 shows a first configuration in which a minimum proximodistal distance is set. By way of comparison, FIG. 13 shows an increased height setting.

A further difference is that the respective ramps 210*a*, 210*a*, and thus also the support surface 110*a* of the articulation component 100*a*, are not stepped in this embodiment. Instead, a surface profiling P is present. The surface profiling P counteracts unwanted slipping of the articulation component 100*a* from the support components 200*a*, 200*a*'.

The embodiment shown in FIGS. 12 and 13 is also manufactured additively from a biocompatible plastic material K. The manufacture of the tibial trial implant 1*a* is here carried out by means of a single (combined) 3D printing process. As a result of the single printing process, the components 100*a*, 200*a*, 200*a'* are connected non-releasably to each other via the guide devices and at the same time are movable relative to each other.

The invention claimed is:

1. A tibial trial implant for use in a knee joint replacement operation, the tibial trial implant comprising:
- an articulation component with an articulation surface configured for articulation with a femoral component, and with a bottom side; and
- at least one support component with a bearing surface configured for bearing on a tibial plateau, a proximal top side forming a ramp inclined relative to the bearing surface, and a guide device having a guide track extending longitudinally parallel to the ramp,
- the bottom side of the articulation component comprising a support surface inclined parallel to the ramp,
- the articulation component being held on the guide device and supported with the support surface on the ramp in a manner linearly movable along the guide track relative to the at least one support component, and
- a relative movement between the articulation component and the at least one support component causing a change in a proximodistal distance between the articulation surface of the articulation component and the bearing surface of the at least one support component.

2. The tibial trial implant according to claim 1, wherein the ramp and/or the support surface is flat and has a surface profiling configured to counteract slipping of the articulation component from the ramp.

3. The tibial trial implant according to claim 1, wherein the ramp and the support surface are each provided with a sequence of steps, whereby the relative movement between the articulation component and the at least one support component causes a step-by-step change in the proximodistal distance.

4. The tibial trial implant according to claim 3, wherein the steps each have a proximodistal height of between 1 mm and 3 mm, with at least four steps each being present.

5. The tibial trial implant according to claim 3, wherein the steps of the ramp each have a convex protuberance, and the steps of the support surface each have a concave indentation, wherein the convex protuberances and the concave indentations engage releasably in one another, thereby counteracting an unwanted relative movement between the articulation component and the at least one support component.

6. The tibial trial implant according to claim 1, wherein the ramp and/or the support surface has a longitudinal inclination of 10° to 45°.

7. The tibial trial implant according to claim 1, wherein the ramp and the support surface are longitudinally inclined in an anteroposterior direction.

8. The tibial trial implant according to claim 1, wherein the ramp and the support surface are longitudinally inclined in a mediolateral direction.

9. The tibial trial implant according to claim 8, wherein the at least one support component comprises two support components arranged on both sides of a sagittal median longitudinal plane of the articulation component, wherein the two support components, in order to change the proximodistal distance, are movable mediolaterally in opposite directions relative to the articulation component.

10. The tibial trial implant according to claim 1, wherein the guide device has at least one guide slot, in which at least one guide pin of the articulation component engages slidably along the guide track.

11. The tibial trial implant according to claim 10, wherein the at least one guide slot has, at one end of the guide track, an insertion opening which, starting from the bearing surface, opens into the at least one guide slot substantially perpendicularly to the guide track, and through which the at least one guide pin is insertable into the at least one guide slot.

12. The tibial trial implant according to claim 1, wherein the support surface is recessed proximally into the bottom side of the articulation component and bounded by opposite wall sections, which in each case bear with a form-fit on the at least one support component perpendicularly to the guide track and perpendicularly to a proximodistal axis.

13. The tibial trial implant according to claim 1, wherein the articulation component has a recess which extends proximodistally from the articulation surface to the support surface and which divides the articulation surface and the support surface into in each case a medial surface section and a lateral surface section.

14. The tibial trial implant according to claim 1, wherein the at least one support component has a recess which extends proximodistally through the ramp and which divides the ramp into two ramp sections, the two ramp sections being spaced apart from each other laterally.

15. The tibial trial implant according to claim 14, wherein the at least one support component, seen in a proximal and/or distal viewing direction, has a U-shape, wherein the two ramp sections each form an elongate leg of the U-shape.

16. The tibial trial implant according to claim 1, wherein the articulation component and the at least one support component are each manufactured from a biocompatible plastic material.

17. The tibial trial implant according to claim 1, wherein the articulation component and the at least one support component are additively manufactured by a single 3D printing process, whereby the articulation component and the at least one support component are connected non-releasably to each other via the guide device and are movable relative to each other.

* * * * *